(12) United States Patent
Chong et al.

(10) Patent No.: US 10,496,700 B2
(45) Date of Patent: *Dec. 3, 2019

(54) MOTION-BASED MUSIC RECOMMENDATION FOR MOBILE DEVICES

(71) Applicant: Futurewei Technologies, Inc., Plano, TX (US)

(72) Inventors: Chia-Chin Chong, Palo Alto, CA (US); Jianyu Zhang, San Jose, CA (US)

(73) Assignee: Futurewei Technologies, Inc., Plano, TX (US)

(*) Notice: Subject to any disclaimer, the term of this patent is extended or adjusted under 35 U.S.C. 154(b) by 403 days.

This patent is subject to a terminal disclaimer.

(21) Appl. No.: 15/250,347

(22) Filed: Aug. 29, 2016

(65) Prior Publication Data

US 2016/0371371 A1 Dec. 22, 2016

Related U.S. Application Data

(63) Continuation of application No. 14/040,436, filed on Sep. 27, 2013, now Pat. No. 9,454,604.

(Continued)

(51) Int. Cl.
| | | |
|---|---|---|
| *A61B 5/00* | (2006.01) | |
| *A61B 5/01* | (2006.01) | |
| *A61B 5/11* | (2006.01) | |
| *G06F 3/16* | (2006.01) | |
| *A63B 24/00* | (2006.01) | |

(Continued)

(52) U.S. Cl.
CPC ......... *G06F 16/636* (2019.01); *A61B 5/1118* (2013.01); *G06F 3/16* (2013.01); *G06F 3/165* (2013.01); *G06F 16/635* (2019.01); *G06F 16/639* (2019.01); *G06F 16/686* (2019.01); *G06F 16/90324* (2019.01); *G06N 20/00* (2019.01); *H04H 60/33* (2013.01); *H04H 60/46* (2013.01); *H04H 60/49* (2013.01); *H04H 60/65* (2013.01); *A61B 5/01* (2013.01); *A61B 5/02055* (2013.01); *A61B 5/0402* (2013.01);

(Continued)

(58) Field of Classification Search
CPC .............. G06F 3/165; G06F 17/30749; G06F 17/30761; G06F 17/30764; G06F 17/30766; G06F 17/30769; G10L 25/63; H04H 60/12; H04H 60/16; H04H 60/33; H04H 60/35; H04H 60/45; H04H 60/46; H04H 60/49; H04H 60/59; H04H 60/65; A63B 24/0062
USPC .......................................................... 700/94
See application file for complete search history.

(56) References Cited

U.S. PATENT DOCUMENTS

| | | |
|---|---|---|
| 8,442,969 B2 | 5/2013 | Gross |
| 2002/0041692 A1 | 4/2002 | Seto et al. |

(Continued)

OTHER PUBLICATIONS

"Musicovery," downloaded from http://en.wikipedia.org/wiki/Musicovery on Sep. 27, 2013, 4 pgs.

(Continued)

*Primary Examiner* — Jesse A Elbin
(74) *Attorney, Agent, or Firm* — Conley Rose, P.C.

(57) ABSTRACT

A method comprising acquiring a plurality of measurements from at least one sensor in a mobile device, determining an activity classification of a user of the mobile device based on the plurality of measurements, acquiring an audio file for the mobile device, wherein the audio file is selected based on the activity classification, and playing the audio file by the mobile device.

17 Claims, 10 Drawing Sheets

Related U.S. Application Data

(60) Provisional application No. 61/800,380, filed on Mar. 15, 2013.

(51) Int. Cl.

| | | |
|---|---|---|
| *G06F 16/68* | (2019.01) | |
| *G06N 20/00* | (2019.01) | |
| *A61B 5/0205* | (2006.01) | |
| *A61B 5/0402* | (2006.01) | |
| *A61B 5/0476* | (2006.01) | |
| *G06F 16/635* | (2019.01) | |
| *G06F 16/638* | (2019.01) | |
| *G06F 16/9032* | (2019.01) | |
| *H04H 60/49* | (2008.01) | |
| *H04H 60/33* | (2008.01) | |
| *H04H 60/46* | (2008.01) | |
| *H04H 60/65* | (2008.01) | |

(52) U.S. Cl.
CPC ........... *A61B 5/0476* (2013.01); *A61B 5/4806* (2013.01); *A63B 24/0062* (2013.01); *G06F 16/68* (2019.01)

(56) References Cited

U.S. PATENT DOCUMENTS

| | | |
|---|---|---|
| 2007/0113725 A1 | 5/2007 | Oliver et al. |
| 2008/0096726 A1 | 4/2008 | Riley et al. |
| 2009/0006288 A1 | 1/2009 | Yamamoto |
| 2009/0069912 A1 | 3/2009 | Stefik |
| 2009/0076637 A1 | 3/2009 | Kameyama |
| 2011/0093100 A1 | 4/2011 | Ramsay |
| 2011/0169603 A1 | 7/2011 | Fithian et al. |
| 2012/0229270 A1 | 9/2012 | Morley et al. |
| 2014/0119564 A1 | 5/2014 | Caskey et al. |

OTHER PUBLICATIONS

"Pandora Radio," downloaded from http://en.wikipedia.org/wiki/Pandora_Radio on Sep. 27, 2013, 10 pgs.

"Spotify," downloaded from http://en.wikipedia.org/wiki/Spotify on Sep. 27, 2013, 17 pgs.

"User:Yuhamidaru/stereomood," downloaded from http://en.wikipedia.org/wiki/User:Yuhamidaru/stereomood on Sep. 27, 2013, 3 pgs.

Shardanand, U., "Social Information Filtering for Music Recommendation," Massachusetts Institute of Technology, Sep. 1994, pp. 1-93.

Kuo, F.-F., "Emotion-based Music Recommendation by Association Discovery from Film Music," MM'05 Nov. 6-11, 2005, Singapore, 2005 ACM, pp. 507-510.

Fitchard, K., "How Gracenote is building a Car Stereo that senses your driving mood," downloaded from http://gigaom.com/2013/02/19/how-gracenote-is-building-a-car-stereo-that-senses-your-driving-mood/ on Sep. 30, 2013, 4 pages.

Office Action dated Sep. 10, 2015, 21 pages, U.S. Appl. No. 14/040,438, filed Sep. 27, 2013.

Notice of Allowance dated May 20, 2016, 8 pages, U.S. Appl. No. 14/040,438, filed Sep. 27, 2013.

Office Action dated Feb. 4, 2016, 22 pages, U.S. Appl. No. 14/040,438, filed Sep. 27, 2013.

Office Action dated Apr. 13, 2016, 5 pages, U.S. Appl. No. 14/040,438, filed Sep. 27, 2013.

Office Action dated Mar. 17, 2016, 20 pages, U.S. Appl. No. 14/040,436, filed Sep. 27, 2013.

Office Action dated Sep. 17, 2015, 22 pages, U.S. Appl. No. 14/040,436, filed Sep. 27, 2013.

Notice of Allowance dated May 20, 2016, 8 pages, U.S. Appl. No. 14/040,436, filed Sep. 27, 2013.

Office Action dated Oct. 16, 2015, 14 pages, U.S. Appl. No. 14/142,249, filed Dec. 27, 2013.

MOTION-BASED MUSIC RECOMMENDATION FOR MOBILE DEVICES

CROSS-REFERENCE TO RELATED APPLICATIONS

The present application is a continuation of U.S. patent application Ser. No. 14/040,436 filed Sep. 27, 2013 by Chia-Chin Chong, et al. and entitled "Motion-Based Music Recommendation for Mobile Devices", which claims priority to U.S. Provisional Patent Application No. 61/800,380 filed Mar. 15, 2013 by Chia-Chin Chong, et al. and entitled "Motion-Based Music Recommendation System, Method and Service for Mobile Devices", both of which are incorporated herein by reference in their entireties.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Music recommendation systems and services such as Pandora, Ringo and Spotify are becoming an increasingly popular way for users to find and listen to music that may be of interest to them. Most of these music recommendation systems identify music for the user to listen to based on the user's personal preferences as indicated by the user through manual selection or some other type of affirmative user action indicating the user's preferences (e.g., "like").

Pandora is free personalized internet radio. The service plays musical selections of a certain genre based on the user's artist selection. The user then provides positive or negative feedback for songs chosen by the service, which are taken into account when Pandora selects or recommends future songs to the user.

Pandora recommends songs based on a certain genre and artist that the user has selected in advanced. Furthermore, the user needs to provide positive or negative feedback for songs chosen by the service, which are taken into account when Pandora selects future songs to further improve the music recommendation system.

Ringo is a music recommendation system accessible to users only via email. Users rate musical artists and then are able to receive recommendations for further listening.

Spotify is a new way to enjoy music socially. Spotify does not recommend songs based on individual preferences, but instead allows registered users to integrate their account with existing Facebook and Twitter accounts. Once a user integrates their Spotify account with other social media profiles, they are able to access their friends' favorite music and playlists. Because music is social, Spotify allows you to share songs and playlists with friends, and even work together on collaborative playlists.

However, existing music recommendation systems and services such as the above are relatively inflexible in that they generally do not take into account the changing music preferences of users of mobile devices (e.g., smartphones) from moment to moment as they engage in different activities or enter different environments. Mobile device users typically use their devices on the go while engaged in various different activities and located in environments in which their music listening preferences may change from moment to moment. Requiring users to manually set or change their personal music listening preferences on their mobile device can be inconvenient as they are constantly changing between different activities or environments, especially considering the limited user interface currently provided by mobile devices.

In view of the above, there is a need for a music recommendation system and service for users of mobile devices such as smartphones that better takes the changing music preferences of the user into account.

SUMMARY

In at least one embodiment, the disclosure includes a method comprising acquiring a plurality of measurements from at least one sensor in a mobile device, determining an activity classification of a user of the mobile device based on the plurality of measurements, acquiring an audio file for the mobile device, wherein the audio file is selected based on the activity classification, and playing the audio file by the mobile device.

In at least one embodiment, the disclosure includes a computer program product comprising computer executable instructions stored on a non-transitory computer readable medium such that when executed by a processor cause a mobile device to acquire a plurality of measurements from at least one sensor in a mobile device, determine an activity classification of a user of the mobile device based on the plurality of measurements, acquire an audio file for the mobile device, wherein the audio file is selected based on the activity classification, and play the audio file by the mobile device.

In at least one embodiment, the disclosure includes a mobile device comprising at least one sensor configured to generate a plurality of measurements, a processor coupled to the at least one sensor and configured to acquire the plurality of measurements, determine an activity classification of a user of the mobile device based on the plurality of measurements, and acquire an audio file, wherein the audio file is selected based on the activity classification.

DETAILED DESCRIPTION

Figure 1:
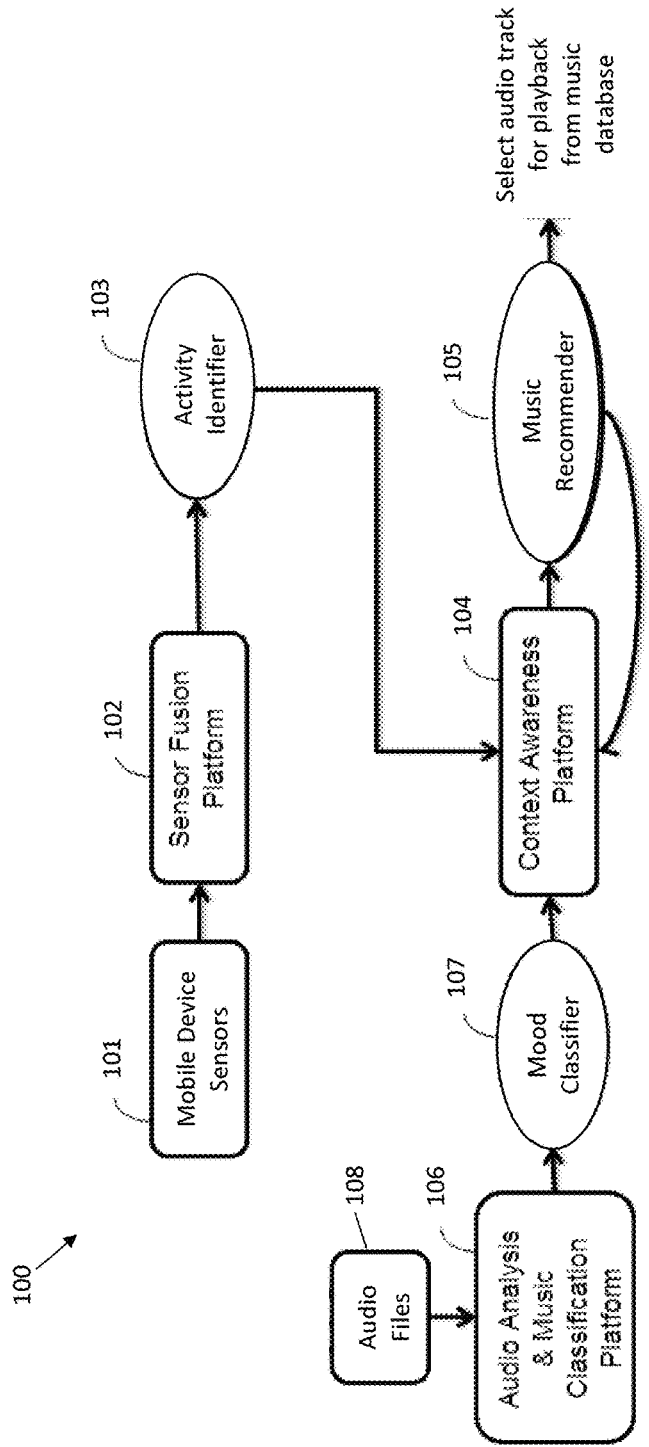
FIG. 1 is a logical view illustrating the structure and function of an embodiment of an automatic personalized music recommendation system.

It should be understood at the outset that, although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents. While certain aspects of conventional technologies have been discussed to facilitate the present disclosure, these technical aspects are in no way disclaimed, and it is contemplated that the present disclosure may encompass one or more of the conventional technical aspects discussed herein.

In view of the limitations of existing music recommendation systems and services as described above, a need is recognized for a personalized music recommendation system, method and service for mobile wireless communication devices (or "mobile devices" for short), such as smartphones or cell phones, that takes the mobile device user's inferred mood or emotions into account.

In at least some embodiments, the disclosed music recommendation system exploits the sensors that exist on mobile devices (and other wearable devices that can be connected with mobile devices) and combines them with mood-based music classification to make personalized music recommendations based on the user's current physical motion and inferred activities and/or mood. The system maps physical motion with the user's mood through the use of a context awareness platform learning system.

The type of music or song to be recommended to the user may be based on a mood categories, which can be obtained from a context awareness platform in a mobile device. The context awareness platform may infer a mood of a user from physical activity as measured by one or more sensors in the mobile device. In this manner, this music recommendation method and system quickly and automatically adapts the recommendations based on changes in the user's activities and environment. The disclosed music recommendation system does not require manual intervention or express action by the user and quickly adapts to changes in the user's inferred mood or preferences from moment to moment.

While many of the embodiments are discussed in the context of a mobile device such as a smartphone, it may be implemented on any portable electronic device with physical and/or virtual sensors that is capable of playing music (e.g., Moving Picture Experts Group (MPEG)-1 (MPEG-1) or MPEG-2 Audio Layer III (MP3) player, tablet computer, wrist computer). Also, although in this illustrative embodiment the music recommendation method is implemented in a mobile device, one of ordinary skill in the art could readily implement the method as a cloud-based service for a mobile device. Further, although the illustrative embodiments are described in the context of recommending music content to the user, one of ordinary skill in the art could readily adapt the method to recommending other types of content to the user, such as videos, animated graphics, and web sites.

FIG. 1 is a logical view of the structure and function of an embodiment of an automatic personalized music recommendation system 100. The system 100 includes mobile device sensors 101, sensor fusion platform 102, activity identifier 103, audio analysis/music classification platform 106, mood classifier 107, context awareness platform 104 and music recommender 105, which work together as indicated to automatically provide personalized music recommendations to a user of a mobile device.

The system 100 also includes audio files 108. Each audio file in the audio files 108 may be a recorded song or music. An audio file may be saved in any audio format, such as Advanced Audio Coding (AAC) or MP3. The audio files 108 may be stored in any of a number of locations. For example, some or all of the audio files may be stored locally on a mobile device and some or all of the audio files may be stored in a cloud-based storage application or system.

In addition to audio files 108, at least a portion of the system 100 may be part of the mobile device. A portion of the system 100 may be part of a cloud-based storage and processing system as explained further below.

Sensors 101 are physical sensors that are embedded in the mobile device and are used to obtain data on the physical motion of the user of the mobile device. The mobile device sensors 101 may include accelerometers, magnetometers, gyroscopes, pressure sensors, a Global Positioning System (GPS) device, or any other type of sensor for measuring position and/or orientation of the mobile device. The type of information provided by the listed sensor types are understood by a person of ordinary skill in the art. For example, an accelerometer is commonly used in mobile devices for user interface control. An accelerometer in such an application measures an orientation of the mobile device and may adjust a user interface or display accordingly. Accelerometers may also be used in pedometer applications to measure a number of steps taken by a user. As another example, a magnetometer may use the fact that a direction of the Earth's magnetic field at or near the Earth's surface may be known. The various mobile device sensors 101 provides inputs into the sensor fusion platform 102.

Figure 2:
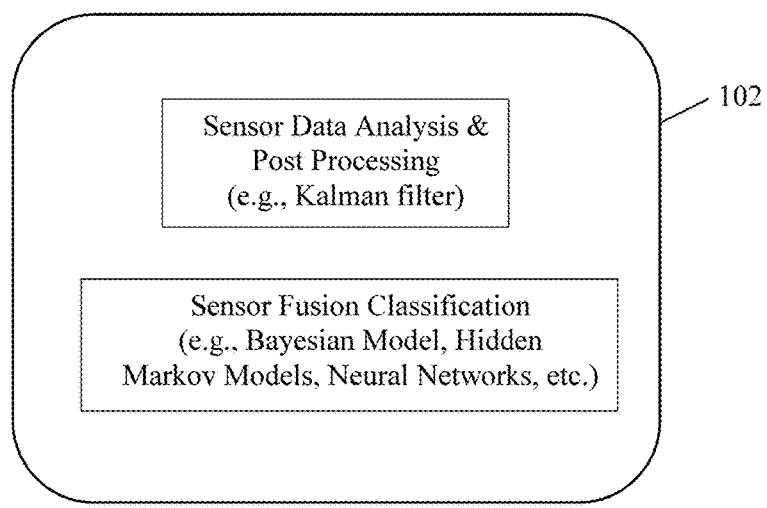
FIG. 2 shows an illustrative embodiment of a sensor fusion platform.

FIG. 2 shows an illustrative embodiment of the sensor fusion platform 102. The sensor fusion platform 102 receives and combines the raw data collected from sensors 101 for input into activity identifier 103. Sensor fusion platform 102 may include sensor data analysis and post-processing and sensor fusion classification. Sensor data analysis may be implemented using a Kalman filter (i.e., linear quadratic estimation) or other type of filtering as is well known in the art. Sensor fusion classification may be implemented using Bayesian models, hidden Markov models, neural networks, etc. The sensor fusion platform 102 may be implemented as a module or computer program instructions in a computing system, such as a mobile device.

Figure 3:
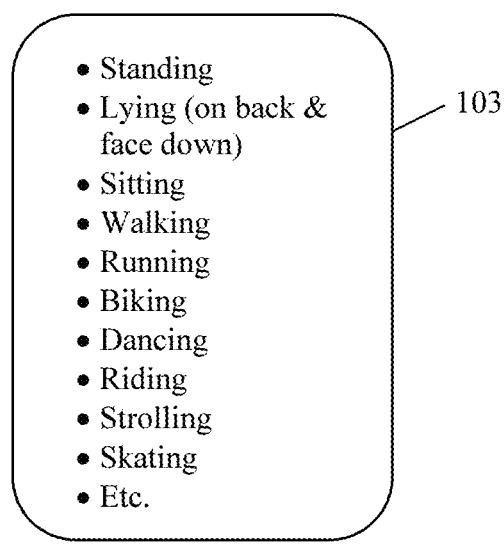
FIG. 3 shows an illustrative embodiment of an activity identifier.
Figure 4:
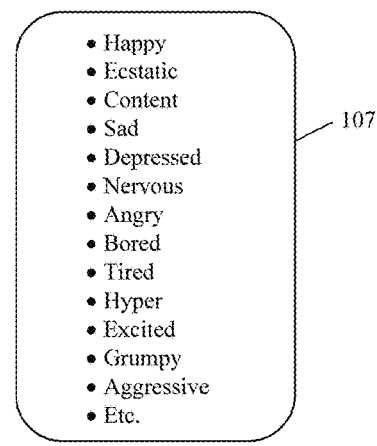
FIG. 4 shows an illustrative embodiment of a music classifier.

FIG. 3 shows an illustrative embodiment of activity identifier 103. Activity identifier 103 is a table of possible physical activities that will be inferred by sensor fusion platform 102 based on sensing data collected from sensors 101. These physical activities may include sitting, walking, running, driving, etc. as shown in FIG. 4. The sensor fusion platform 102 and the activity identifier 103 work together to accept sensor data from sensors 101 in a mobile device and identify an activity of a user of the mobile device based on the sensor data.

FIG. 4 shows an illustrative embodiment of mood classifier 107. Mood classifier 107 is a table of possible moods (or emotional states) that can be used to classify each of the songs or audio files. These moods could include happy, ecstatic, content, sad, depressed, nervous, angry, bored, tired, hyper, excited, grumpy, aggressive, etc. Mood classifier 107 may tag each song or audio file with one or more moods or emotional states that may be based on learning and feedback behavior from context aware platform 104 as explained more fully below.

Figure 5:
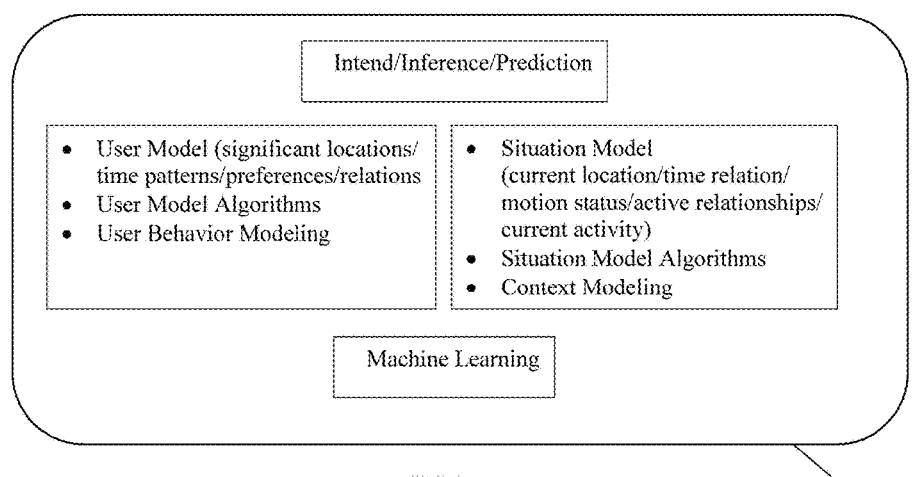
FIG. 5 shows an illustrative embodiment of a conceptual context awareness platform.

FIG. 5 shows an illustrative embodiment of conceptual context awareness platform 104. Context awareness platform 104 may include the following three components: (1) user intent/inference/prediction, (2) user model/situational model and (3) machine learning. The user model component includes: (1) a user model specifying significant locations, time patterns, preferences and relations, (2) user model algorithms and (3) user behavior modeling. The situational model component includes: (1) a situational model specifying current locations, time relation, motion status, active relationships, current activity, (2) situational model algorithms and (3) context modeling.

Figure 6:
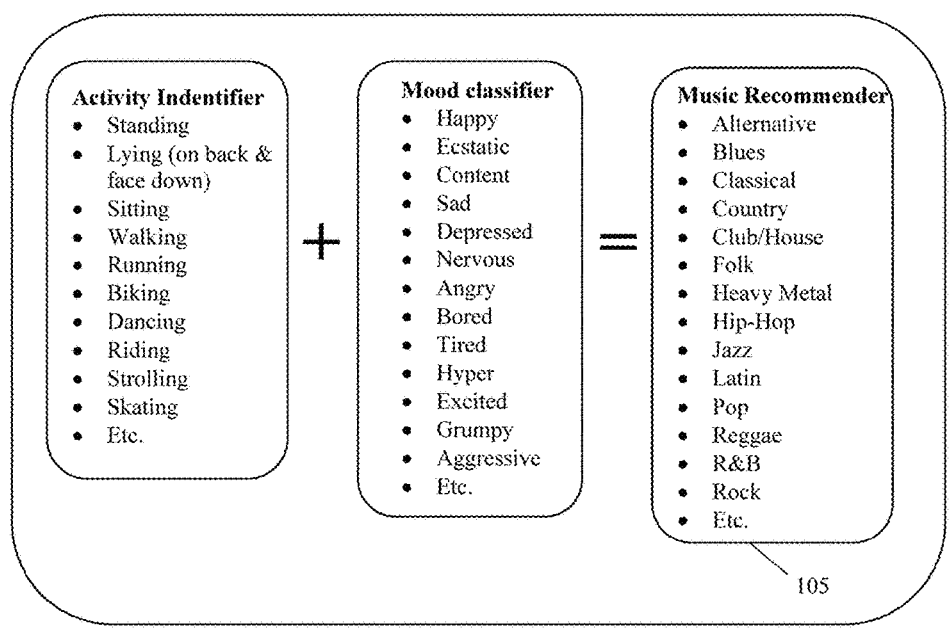
FIG. 6 shows an illustrative embodiment of music recommender.

FIG. 6 shows an illustrative embodiment of music recommender 105. Music recommender 105 is a table of possible music types or genres that are provided as input to context awareness platform 104. These music types could include alternative, blues, classical, etc. Music recommender 105 is a learning system that will improve its recommendation accuracy with time.

Figure 7:
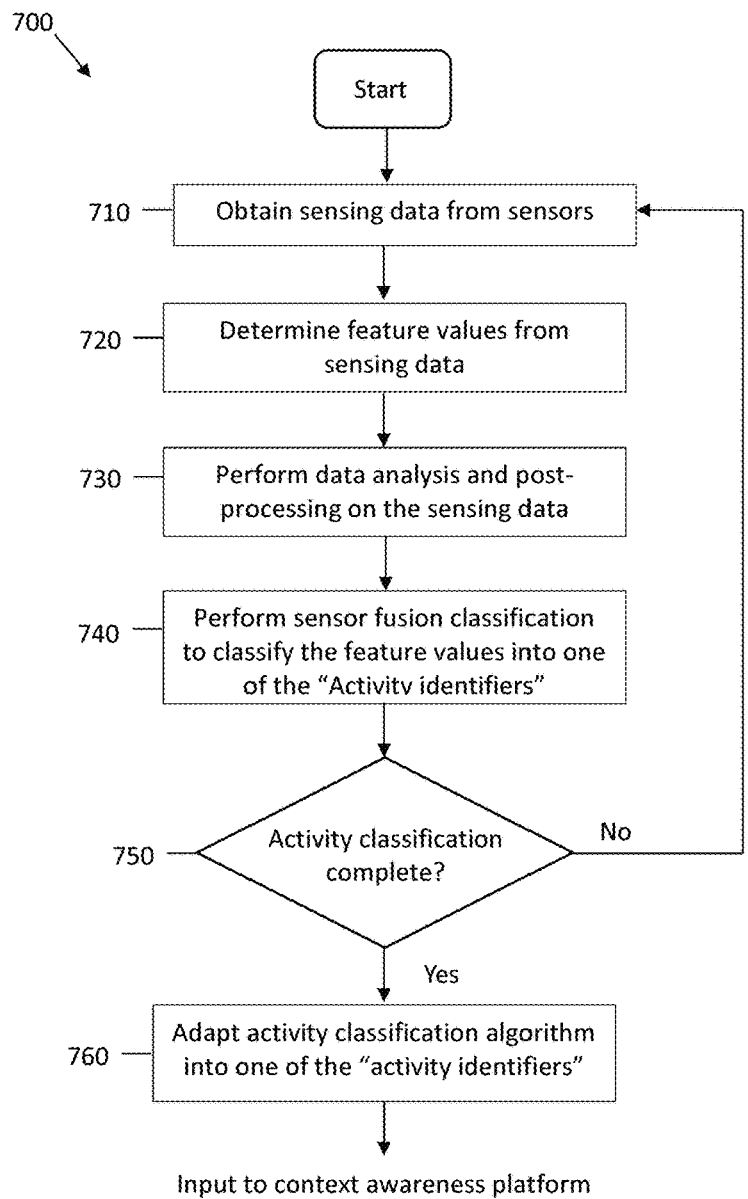
FIGS. 7, 8 and 9 are flowcharts illustrating embodiments of methods for generating music recommendations to the user based on sensor input and user intent/inference/prediction of the context awareness platform.
Figure 8:
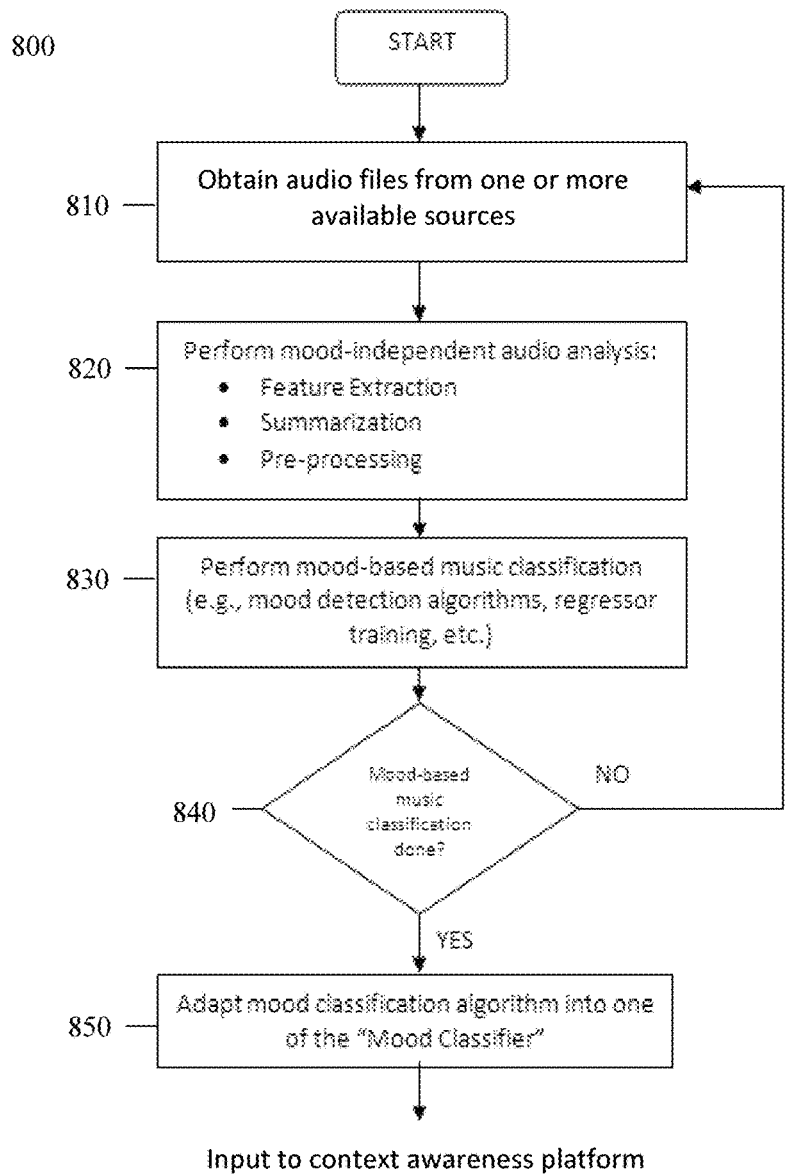
Figure 9:
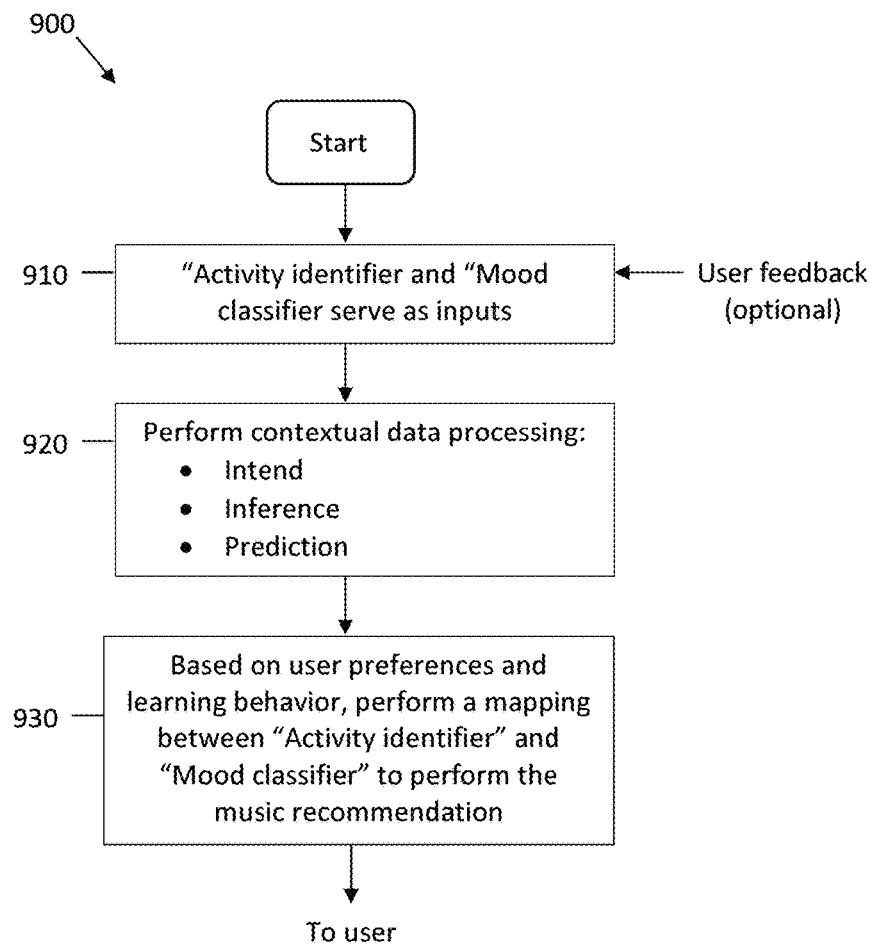

FIGS. 7, 8 and 9 are flowcharts showing the process in which the music recommendation system shown in FIG. 1 generates music recommendations based on sensor input and user intent/inference/prediction of the context awareness platform.

FIG. 7 is a flowchart of an embodiment of a method 700 for classifying motion of a user into an activity classification FIG. 7 illustrates how raw data obtained from sensors 101 of a mobile device may be analyzed and processed by the sensor fusion platform 102 to generate the vector of feature values, which will then be classified by sensor fusion platform 102 into activity identifier 103. In block 710, data is obtained from sensors, such as sensors 101. The data may be position, rotation/orientation, or motion data regarding the mobile device in which the sensors 101 are embedded. Such data may reflect motion of a user of the mobile device. The data may be provided to a sensor fusion platform 102. In block 720, feature values are determined from sensing data. In block 730, data analysis and post-processing of the sensing data may be performed. In this block, Kalman filtering and other signal processing may be performed on the data, e.g., to determine a pattern of speed and/or orientation and/or motion. Feature values of the underlying data may be determined. In block 740, the results of block 730 are used to classify the activity of the user into one of the activity identifiers, e.g., one of the activities listed in FIG. 3. Sensor fusion classification may be performed in block 740, which may involve the construction of Bayesian models, Markov models, and/or neural networks. These are well-known statistical models/methods typically used to process huge amounts of data. A benefit would be the capability of these models to handle large dimensional data. In block 750, a decision is made whether activity classification is complete. A determination of whether it is complete may be based on whether sufficient data has been collected to provide confidence in the activity classification or it may be based on whether a sufficient amount of time has passed since sensor data collection began. If activity classification is complete, block 760 is performed, in which an "activity identifier" is selected. The activity identifier may be one of the activities listed in FIG. 3. The selected activity identifier may be provided as an input to the context awareness platform 104. If activity classification is not complete, the flowchart returns to block 710 in which more sensing data is collected.

FIG. 8 is a flowchart of an embodiment of a method 800 for classifying an audio file into one or more moods. The method 800 shows how audio files, e.g., audio files 108, are obtained & sorted in order to perform both the mood-independent audio analysis & mood-based music classification in audio analysis/music classification platform 106 (or "platform 106"), which will then classified by the platform 106 into mood classifier 107. The method 800 begins in block 810. In block 810, audio files may be obtained from available sources, such as from cloud storage, local storage on a mobile device, etc. The platform 106 may receive one or more audio files as inputs. In block 820, mood-independent audio analysis is performed, which may include feature extraction, summarization, and pre-processing of the audio signal represented by an audio file. In block 830, mood-based music classification may be performed, e.g., using mood detection algorithms or regressor training in order to map or classify an audio file into one or more of the moods in the mood classifier 107. In decision block 840, a decision is made whether mood-based classification is complete. If classification is complete, a mood classifier is selected in block 850 for the audio files. After this process, an audio file will have at least one associated mood. The mood may be one of those shown in FIG. 4. A database of audio file names and associated moods may be created based on the method 800. The platform 106 may perform blocks 810-840.

Note that the method 800 for classifying an audio file into a mood can be performed offline (e.g., using a server or multiple servers in a network) and the database of audio file names and associate moods may be stored using any storage medium local or remote to a mobile device.

FIG. 9 is a flowchart of a method 900 for making a music recommendation. In block 910, an activity identifier (e.g., activity identifier 103) and a mood classifier (e.g., mood classifier 107) may serve as inputs. These inputs may be derived as shown in FIGS. 7 and 8. A context awareness platform may acquire or receive the inputs. In block 920, a machine-learning algorithm is performed that learns how to correlate activity to mood based on user feedback (if any). At the outset before any user feedback, the method 900 includes a set of initial conditions that correlates or maps user activity to mood. In block 930, a mapping of activity identifier to mood classifier is performed which is used to generate a music recommendation. In summary, in at least one embodiment sensor data leads to a user activity classification which maps to a mood which maps to a music genre which provides a music recommendation. FIG. 9 illustrates how an activity identifier 103 and mood classifier 107 may be used as inputs to the context awareness platform 104 in order for the music recommender 105 to generate music recommendations for a user.

Figure 10:
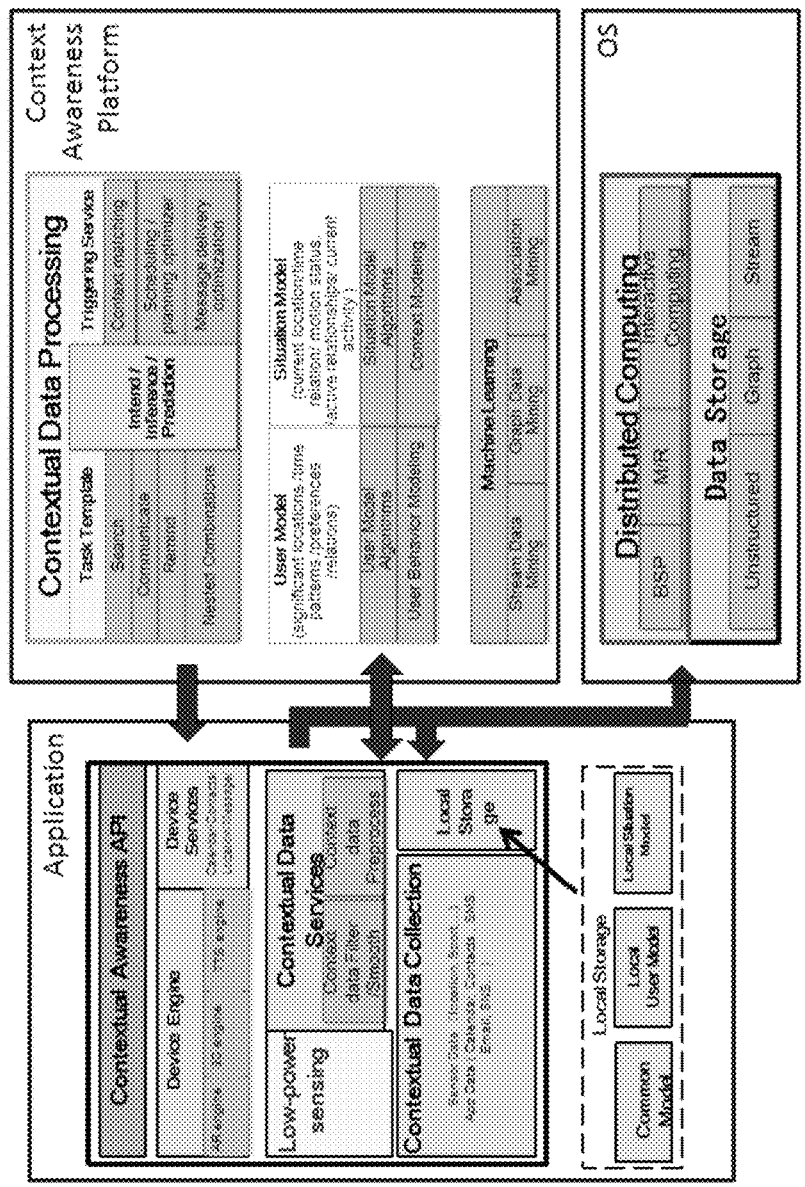
FIG. 10 illustrates an embodiment of a music recommendation system.

FIG. 10 illustrates an embodiment of a music recommendation system, including application (e.g., music recommendation system), context awareness platform, and operating system of the mobile device.

Figure 11:
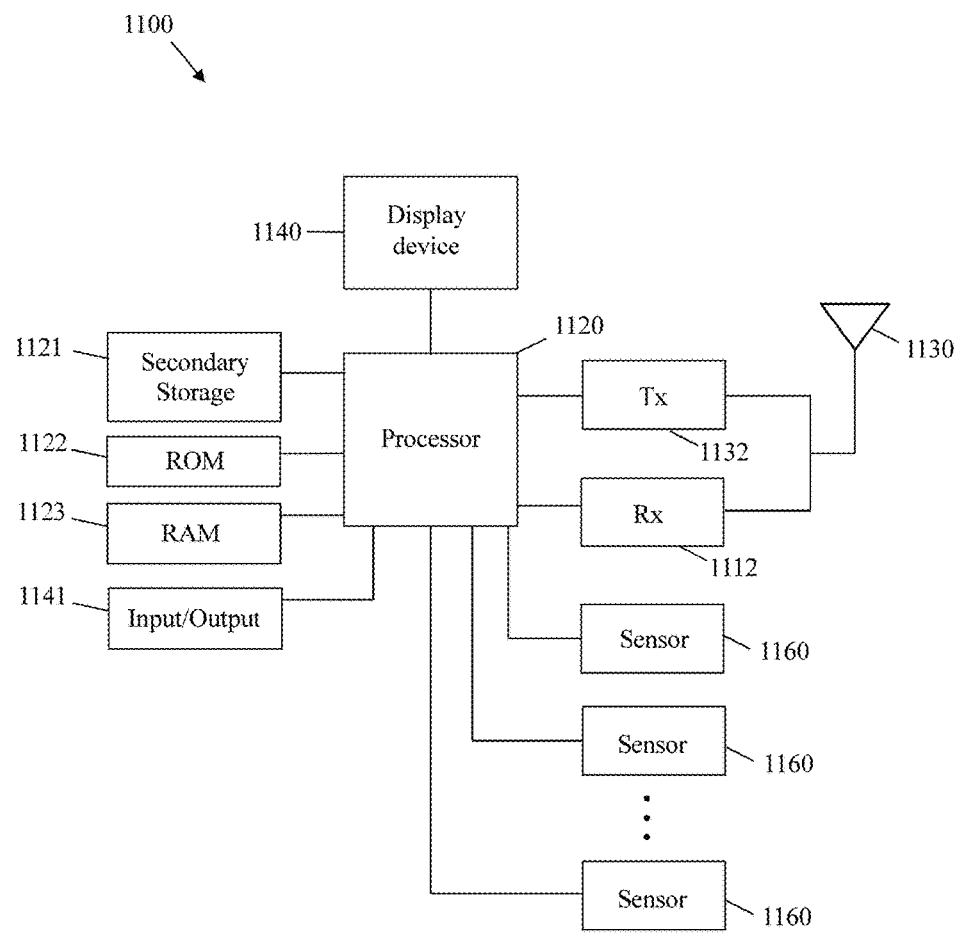
FIG. 11 is a schematic diagram of an embodiment of a mobile device.

FIG. 11 is a block diagram of a mobile device 1100 that may be used to implement the music recommendation method and system disclosed herein. Mobile device 1100 may comprise a processor 1120 (which may be referred to as a central processor unit or CPU) that is in communication with memory devices including secondary storage 1121, read only memory (ROM) 1122, and random access memory (RAM) 1123. The processor 1120 may be implemented as one or more general purpose CPU chips, one or more cores (e.g., a multi-core processor), one or more application specific integrated circuits (ASICs) and/or one or more digital signal processors (DSPs). The processor 1120 may be configured to implement any of the schemes described herein, and may be implemented using hardware, software, firmware, or combinations thereof.

The secondary storage 1121 may be comprised of one or more solid state drives, disk drives, and/or other memory types and is used for non-volatile storage of data and as an over-flow data storage device if RAM 1123 is not large enough to hold all working data. Secondary storage 1121 may be used to store programs that are loaded into RAM 1123 when such programs are selected for execution. The ROM 1122 may be used to store instructions and perhaps data that are read during program execution. ROM 1122 may be a non-volatile memory device that may have a small memory capacity relative to the larger memory capacity of secondary storage 1121. The RAM 1123 may be used to store volatile data and perhaps to store computer instructions. Access to both ROM 1122 and RAM 1123 may be faster than to secondary storage 1121.

The mobile device 1100 may communicate data (e.g., packets) wirelessly with a network via a network access point (not shown). As such, the mobile device 1100 may comprise a receiver (Rx) 1112, which may be configured for receiving data (e.g. wireless packets or frames) from other components. The receiver 1112 may be coupled to the processor 1120, which may be configured to process the data and determine to which components the data is to be sent. The mobile device 1100 may also comprise a transmitter (Tx) 1132 coupled to the processor 1120 and configured for transmitting data to other components, for example by using protocols such as Institute of Electrical and Electronics Engineers (IEEE) 802.11, IEEE 802.16, 3rd Generation Partnership Project (3GPP), Global System for Mobile Communications (GSM), or similar wireless protocols. The receiver 1112 and the transmitter 1132 may be coupled to at least one antenna 1130, which may be configured to receive and transmit wireless radio frequency (RF) signals. In some embodiments, Tx 1132 and Rx 1112 may be replaced by a transceiver comprising the functionality of both Tx 1132 and Rx 1112. If the context awareness platform 104 and logic for selecting an audio file based on activity identifier is located in a cloud-based application, the Tx 1132 may be used to communicate the activity identifier to the cloud-based application. The cloud-based application may return an audio file selection. The audio file selection may be stored on the mobile device in, e.g., secondary storage 1121 or the audio file selection may be stored in a cloud-based storage application. If audio files (e.g., some or all audio files 108) are stored remotely, the Rx 1112 may be used to receive audio files.

The mobile device 1100 may also comprise a display device 1140 coupled to the processor 1120, that displays output thereof. The mobile device 1100 and the display device 1140 may be configured to display representations of data, which may be visible to a user. The display device 1140 may comprise a color super twisted nematic (CSTN) display, a thin film transistor (TFT) display, a thin film diode (TFD) display, an organic light-emitting diode (OLED) display, an active-matrix OLED display, or any other display screen. The display device 1140 may display in color or monochrome and may be equipped with a touch sensor based on resistive and/or capacitive technologies.

The mobile device 1100 may further comprise an input/output (I/O) device 1141 coupled to the processor 1120, which may allow the user to input commands to the mobile device 1100. Although labeled as a single device, the I/O device 1141 may comprise multiple devices. In the case that the display device 1140 comprises a touch sensor, the display device 1140 may also be considered the I/O device 1141. In addition to and/or in the alternative, an I/O device 1141 may comprise a mouse, trackball, built-in keyboard, external keyboard, and/or any other device that a user may employ to interact with the mobile device 1100. The I/O device 1141 may comprise one or more speakers or headset jacks for providing audio signals. The processor 1120 may convert a digital audio file to an analog audio signal for transmission via the I/O device 1141 to be enjoyed by a user.

The mobile device 1100 may further comprise one or more sensors 1160, such as the sensors 101 described previously. The sensors 1160 may include accelerometers, magnetometers, gyroscopes, pressure sensors, and/or a GPS device as examples. The sensors 1160 provide sensor data to the processor 1120.

It is understood that by programming and/or loading computer executable instructions onto the mobile device 1100, at least one of the processor 1120, memory 1121-1123, and/or Rx/Tx 1112/1132 are changed, transforming the mobile device 1100 in part into a particular machine or apparatus, e.g., a sensor fusion platform 102, an activity identifier 103, a context awareness platform 104, a music recommender 105, an audio analysis and music classification platform 106, and/or a mood classifier 107 as described herein. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an ASIC, because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

What is claimed is:

1. A method comprising:
    acquiring a plurality of measurements of a mobile device from at least one sensor in the mobile device;
    determining an activity classification of a user of the mobile device based on the plurality of measurements, the activity classification identifying an activity of a plurality of activities;
    mapping the activity to a mood from a plurality of moods, wherein an audio file obtained by the mobile device is associated with the mood; and
    playing the audio file associated with the mood to the user through an output of the mobile device, wherein the audio file is selected based on the activity classification and the mood.

2. The method of claim 1, wherein the mobile device stores a mapping of each of a plurality of activity classifications to a corresponding one of the plurality of moods.

3. The method of claim 2, wherein the mapping is pre-determined.

4. The method of claim 3, wherein the mobile device receives a feedback from a user input signal about the audio file, wherein the mapping is adjusted based on the feedback, and wherein a new audio file is selected based on the adjusted mapping.

5. The method of claim 1, wherein selecting the audio file comprises retrieving the audio file from a database, wherein the database stores the plurality of moods and a plurality of audio files for each of the plurality of moods.

6. The method of claim 1, wherein the plurality of measurements comprises a plurality of position measurement values, and wherein determining the activity classification comprises analyzing the plurality of position measurement values to determine the activity classification.

7. The method of claim 1, wherein the plurality of activities comprises one or more of standing, sitting, lying down, walking, running, biking, dancing, riding, strolling, and skating.

8. A computer program product comprising computer executable instructions stored on a non-transitory computer readable medium such that when executed by a processor cause a mobile device to:
   acquire a plurality of measurements of a mobile device from at least one sensor in the mobile device;
   determine an activity classification of a user of the mobile device based on the plurality of measurements, the activity classification identifying an activity of a plurality of activities;
   map the activity to a mood from a plurality of moods, wherein an audio file obtained by the mobile device is associated with the mood; and
   play the audio file associated with the mood to the user through an output of the mobile device, wherein the audio file is selected based on the activity classification and the mood.

9. The computer program product of claim 8, wherein the mobile device stores a mapping of each of a plurality of activity classifications to a corresponding one of the plurality of moods.

10. The computer program product of claim 9, wherein the mobile device receives a feedback from a user input signal about the audio file, wherein the computer program product further comprises instructions to:
   adjust the mapping based on the feedback; and
   select a new audio file based on the adjusted mapping.

11. The computer program product of claim 8, wherein the plurality of measurements comprises a plurality of position measurement values, wherein determining the activity classification comprises analyzing the plurality of position measurement values to determine the activity classification.

12. A mobile device comprising:
   at least one sensor configured to generate a plurality of measurements;
   a processor coupled to the at least one sensor and configured to:
      acquire the plurality of measurements of the mobile device from the at least one sensor;
      determine an activity classification of a user of the mobile device based on the plurality of measurements, the activity classification identifying an activity of a plurality of activities;
      map the activity to a mood from a plurality of moods, wherein an audio file obtained by the mobile device is associated with the mood; and
      play the audio file associated with the mood to the user through an output of the mobile device, wherein the audio file is selected based on the activity classification and the mood.

13. The mobile device of claim 12, wherein the processor coupled to an audio output device, and wherein the processor is further configured to:
   convert the audio file into a signal for use by the audio output device and send the signal to the audio output device.

14. The mobile device of claim 12, further comprising a memory configured to store a mapping of each of a plurality of activity classifications to a corresponding one of the plurality of moods.

15. The mobile device of claim 14, further comprising:
   a touch screen configured to receive a feedback from a user input signal about the audio file, wherein the processor is further configured to:
      adjust the mapping based on the feedback; and
      select a new audio file based on the adjusted mapping.

16. The mobile device of claim 15, wherein the at least one sensor comprises an accelerometer, wherein the plurality of measurements comprises a plurality of accelerometer measurement values, and wherein determining the activity classification comprises analyzing the plurality of accelerometer measurement values to determine the activity classification.

17. The mobile device of claim 12, wherein the plurality of activities comprises one or more of standing, sitting, lying down, walking, running, biking, dancing, riding, strolling, and skating.

* * * * *